United States Patent [19]

Wohlgemuth

[11] Patent Number: 5,567,154

[45] Date of Patent: Oct. 22, 1996

[54] DENTAL TURBINE DRIVE HAVING MEANS FOR AUTOMATIC SPEED CONTROL

[75] Inventor: Juergen Wohlgemuth, Darmstadt, Germany

[73] Assignee: Siemens Aktiengesellschaft, Munich, Germany

[21] Appl. No.: 505,759

[22] Filed: Jul. 21, 1995

[30] Foreign Application Priority Data

Aug. 8, 1994 [DE] Germany ............................ 44 28 039.4

[51] Int. Cl.$^6$ ..................................................... A61C 1/05
[52] U.S. Cl. ............................................ 433/132; 415/904
[58] Field of Search .................................. 433/132, 106; 415/904, 25, 35

[56] References Cited

U.S. PATENT DOCUMENTS

| 3,189,999 | 6/1965 | Reiter . | |
|---|---|---|---|
| 3,578,872 | 5/1971 | McBurnie | 433/106 |
| 3,865,505 | 2/1975 | Flatland | 415/904 |
| 5,364,227 | 11/1994 | Franetzki et al. | 415/35 |

FOREIGN PATENT DOCUMENTS 4320532  9/1994  Germany .

*Primary Examiner*—Cary E. O'Connor
*Attorney, Agent, or Firm*—Hill, Steadman & Simpson

[57] ABSTRACT

A dental turbine drive contains a rotor disk which is mounted for rotation in a rotor chamber in a head housing of a dental handpiece and is driven by compressed air from a nozzle in the known way. A control element for regulating the speed is arranged in the flow path of the exhaust air and is constructed to change shape or position upon rotation of the rotary disk as a consequence of centrifugal force so that the effective cross section of the exhaust path decreases with increasing speeds and will increase with decreasing speeds. In addition, an additional or second element is provided and includes a pressure chamber connected by channels to the rotor chamber so that the additional element will respond to changes in the pressure in the rotor chamber to support the effect of the control element. The second element can be a diaphragm valve having a valve member extending into either an exhaust channel or a delivery channel. The additional or second element can be a disk coacting with a resilient ring of the control element to form the control chamber in a recess on the rotor which receives the control element.

11 Claims, 3 Drawing Sheets

DENTAL TURBINE DRIVE HAVING MEANS FOR AUTOMATIC SPEED CONTROL

BACKGROUND OF THE INVENTION

The present invention is directed to a dental turbine drive which contains a rotor disk mounted for rotation by bearings in a housing of a handpiece. The rotor disk has a plurality of turbine paddles or blades which are charged with compressed air via a nozzle disposed in the housing, and the turbine drive includes control means for governing the speed of the rotor, which control means is disposed in the flow path of the exhaust air.

U.S. Pat. No. 3,865,505 discloses a turbine drive with control means, wherein a valve that is controlled dependent on the volume throughput of the returned air is arranged in the delivery channel of the compressed drive air. When the speed of the turbine drops due to an external moment, such as a load being applied to the turbine, the valve in the delivery channel is then opened and a greater air volume is conducted to the rotor disk of the turbine as a result of this operation. The regulation of the admission air or the delivery channel is dependent on the return air and can occur in various ways in the known turbine, including a spring-loaded slide in the return air channel that controls the valve in the admission air channel or by a diaphragm/aneroid diaphragm arranged in a return air channel that adjusts a piston that controls the flow in the admission air channel or line. The speed can be kept constant independent of the load with this known control means. Among other things, the apparatus is affected by the disadvantage that relatively great forces that can be exerted in the exhaust air channel only upon utilization of the volume and mass are required for throttling the overall airstream. Therefore, an unstable control behavior of the turbine is created. In addition, the known apparatus requires a relatively large structure inside the turbine handpiece and problems with integration of the control into the handle may occur.

U.S. Ser. No. 08/261,149, filed Jun. 14, 1994, whose disclosure is incorporated herein by reference thereto and which claims priority from the same German Application resulting in German Patent 43 20 532, discloses a dental turbine drive, wherein an adjustment or control means is arranged on the rotating part of the rotor disk for governing the speed. This adjustment means changes its shape and/or position upon rotation of the rotor disk as a consequence of the centrifugal forces that are applied thereto and will change the effective cross section of a discharge channel with increasing speeds causing a decrease in the effective cross section and decreasing speeds causing an increase in the effective cross section.

The control procedure is essentially based on the fact that the actuating power required for regulating results from the speed-dependent centrifugal forces that act on the inherently passive control element arranged on the rotor so that the effective flow cross section for the airstream is varied based on changes in the speed. Given a prescribed, rated speed, the maximum actuating powers and regulating distance that can be achieved can only be influenced via the mechanical properties of the control element, which include the mass, the modulus of elasticity and shape. Therefore, the control element can be influenced to only a limited extent. This is especially true given the employment of commercially standard elastically deformable rings, such as O-rings. The deviation from the desired rated speed that occurs can be relatively great under certain circumstances.

SUMMARY OF THE INVENTION

An object of the present invention is to achieve an improvement in a control means utilizing a control element which will vary the effective flow cross section of the exhaust gas opening dependent on the speed of the rotor, which improvement keeps the deviations as small as possible.

In order to accomplish these goals, the present invention is directed to an improvement in a dental handpiece having a turbine drive including a rotor disk having a plurality of blades on a circumference thereof, said rotor disk being mounted for rotation on an axis in a turbine or rotor disk chamber of a housing of the handpiece with the blades being positioned to be charged with an inflow of compressed air from a nozzle located in the housing and adjustment or first means being disposed in the flow path of the exhaust air for regulating or controlling the turbine speed. The improvements are that the adjustment or first means includes an elastic control element being arranged on the rotor disk in the flow path of the exhaust air, said control element deforming under the influence of the centrifugal forces dependent on the speed and, therefore, constricting the effective flow cross section with increasing speeds and enlarging the effective flow cross section with decreasing speeds so that the air pressure in the part of the rotor chamber facing toward the driving air nozzle raises and/or drops corresponding to the throttle effect and additional means for aiding the first means including a part of the rotor disk chamber facing toward the air nozzle is connected via a channel to an additional chamber that is at least partially limited by a second element that will yield under pressure so that a change in pressure in the rotor disk chamber that acts on said second element produces a movement in said element that supports the effect of the control element.

According to the invention, the part of the rotor disk chamber facing toward the drive air is connected via channels to the additional chamber that is at least partially limited by the second element that yields under pressure, namely such that a change in pressure in the rotor disk chamber that acts on the second element produces a movement of the element that supports the effect of the control element. The direct effect of the centrifugal force used for regulating is reinforced by the additional action of the compressed air present in the drive system. The second element that acts on the control element and generates an additional force component can, in a preferred embodiment, be an elastic membrane that, together with the control element, limits a membrane chamber into which compressed air from the rotor chamber is conveyed via the connecting channel. The intensification of the control realized via the air pressure in the rotor chamber acts dependent on the throttling of the exhaust airstream produced by the control element and, thus, also acts dependent on the speed deviation. The membrane can be composed of a spring steel and can be mechanically connected to the control element. Additional embodiments of the improvement have a membrane disposed in an additional chamber, which membrane actuates a valve element disposed in one of said inlet and outlet channels for the turbine.

Other advantages and features of the invention will be readily apparent from the following description of the preferred embodiments, the drawings and claims.

DESCRIPTION OF THE PREFERRED EMBODIMENTS

Figure 1:
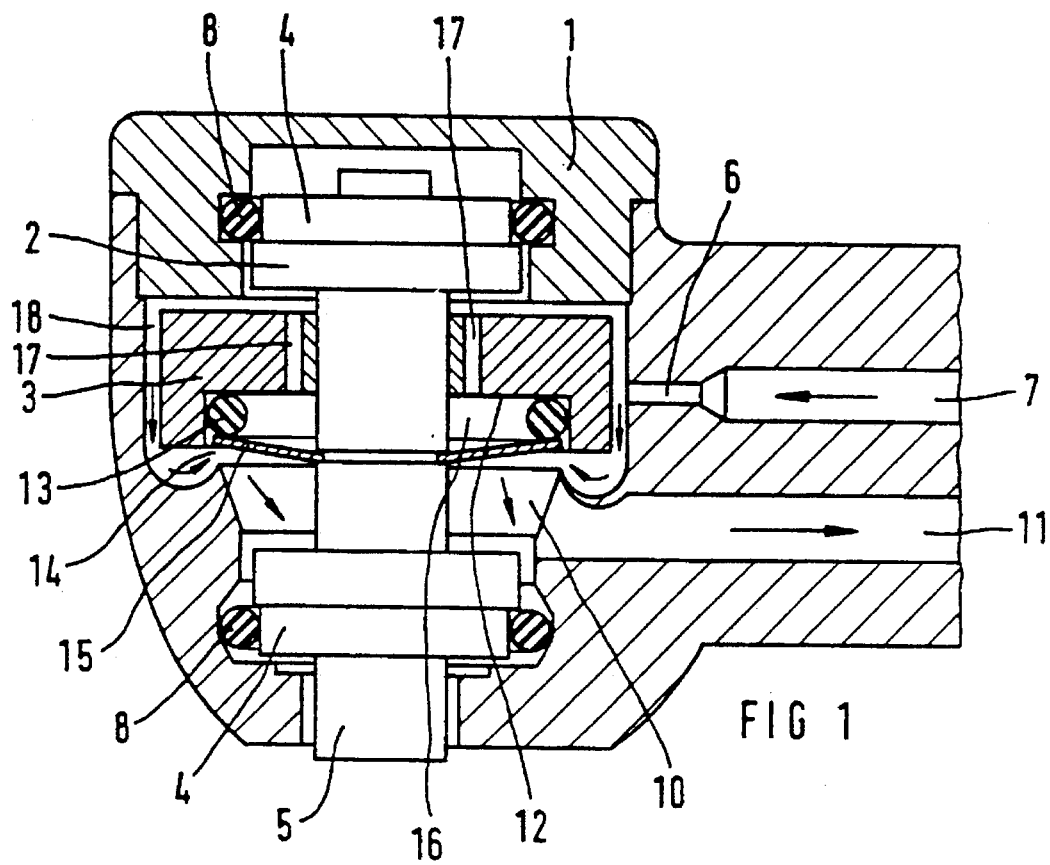
FIG. 1 is a cross sectional view with portions in elevation of a head housing of a dental handpiece having control means in accordance with the present invention.

The principles of the present invention are particularly useful when incorporated in a dental handpiece having a head housing 1 containing a turbine drive unit 2. The turbine drive unit 2 contains a rotor disk 3 that is mounted on a shaft 5 and has a plurality of turbine paddles or blades on a circumference. The shaft 5 is mounted in the housing 1 by bearings 4 so that the rotor can rotate when charged with a compressed air from a delivery channel 7 through a nozzle 6, which directs the air tangentially onto the periphery of the rotor in a known jet principle. An overall drive unit 2 is fixed vibration-dampened in the head housing with elastic rings 8. The delivered compressed air is conducted via an outflow channel 10 into a return air channel 11 after streaming through the turbine blades.

Figure 2:
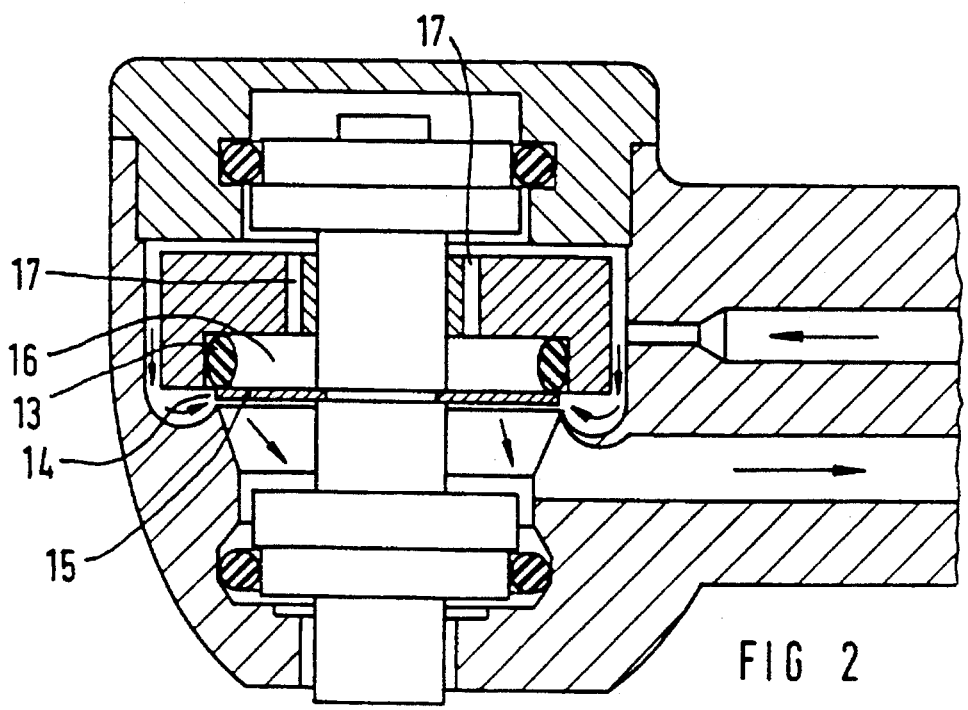
FIG. 2 is a cross sectional view of the embodiment of FIG. 1 with the control means being energized to constrict the cross section of the exhaust channel.

The rotor disk 3 contains a recess 12 which faces toward the outflow channel 10. The recess 12 proceeds concentrically with the shaft 5 and receives an elastic ring 13, which may be an O-ring, which forms a control element for automatically governing the speed. The elasticity of the ring 13 is selected so that its shape and/or position in the recess 12 changes due to the influence of the centrifugal force so that the effective cross section of an annular gap 14 of the outflow channel 10 is diminished in size at higher speeds and is enlarged given a decreasing speed. To this end, the ring 13 is placed in the recess so that it is pressed against the outside wall of the recess. The circular cross section in the quiescent condition changes to an oval, as illustrated in FIG. 2, with increasing speed and, as a result of this, the annular gap 14 between the rotor disk and the housing that forms the effective cross section is reduced in size.

An elastic membrane 15 is secured to the rotor shaft 5, and this membrane has peripheral walls or surfaces lying against the ring 13. The membrane 15 together with the ring 13 and the rotor disk form a membrane chamber 16 that is connected by axial channels 17 in the rotor disk that will proceed parallel to the axis of the rotor shaft 5. The membrane chamber 16 is sealed off from the outflow channel by the elastic membrane 15. As a consequence of the connection of the rotor chamber to the membrane chamber 16, changes in the pressure in the rotor chamber act on the membrane in that the latter, as shown in FIGS. 1 and 2, is adjusted in the axial direction with increased speeds. The effect produced by the centrifugal force, which results in deformation of the ring 13, is additionally intensified by the isodirected membrane force.

The membrane can be fabricated of a suitable spring steel or of a rubber-elastic material as well, for example of silicone material. Expediently, the elasticity of the two parts is matched so that the parts are in contact with one another. The membrane 15 can also be pressed against the ring 13 with a certain prestress. It is also advantageous when the ring 13 and the membrane 15 are connected to one another by a suitable connection, such as by welding, gluing, etc. In addition, the ring 13 and membrane 15 may be formed as a one-piece member.

Figure 3:
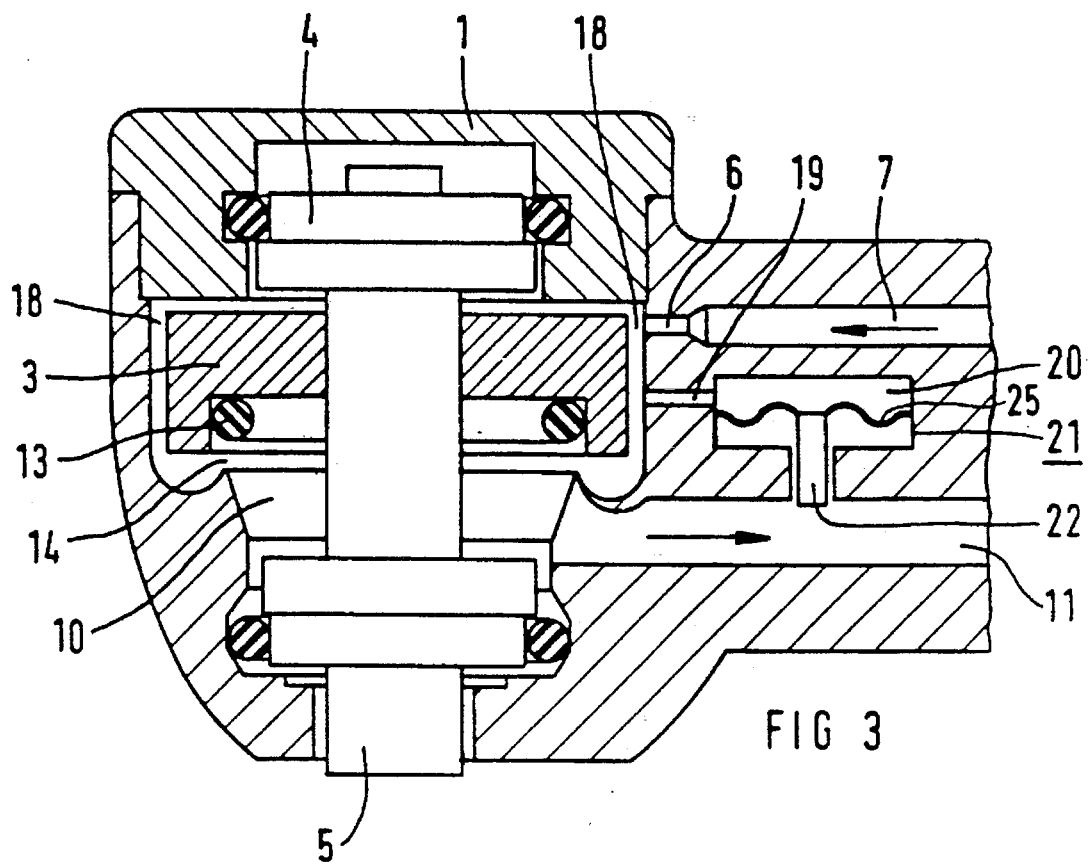
FIG. 3 is a cross sectional view of a head housing of a dental handpiece having a second embodiment of the control means of the present invention.
Figure 4:
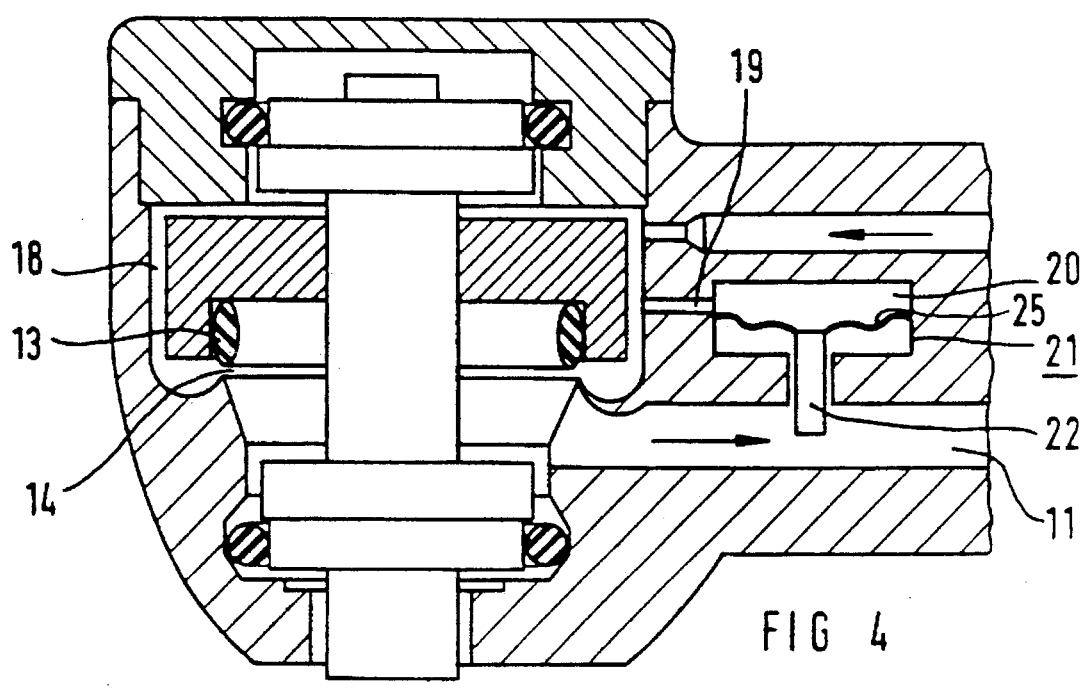
FIG. 4 is a cross sectional view of the embodiment of FIG. 3 with the control means constricting the flow through the exhaust channel.

A second embodiment is illustrated in FIGS. 3 and 4, and this embodiment has an internal pressure of the rotor chamber 18 acting on a throttle valve 21 with which the return airstream can be throttled. Here, the throttle valve is fashioned as a diaphragm valve, wherein the upper chamber 20 is connected to the rotor chamber 18 via a connecting line or channel 19. The cross section of the return air or exhaust air channel 11 can be varied with the control element 22 that is connected to the diaphragm 25 and projects into the return air channel 11. When, for example, given increased speeds, the air pressure in the rotor chamber rises, this will cause an increase in the constriction of the cross section of the channel 11, as illustrated in FIG. 4, via the throttle location when the rated speed is reached and, thus, effects an intensification of the desired speed regulation. The O-ring thereby acts as a pre-control for the throttle location at the throttle valve 21.

Figure 5:
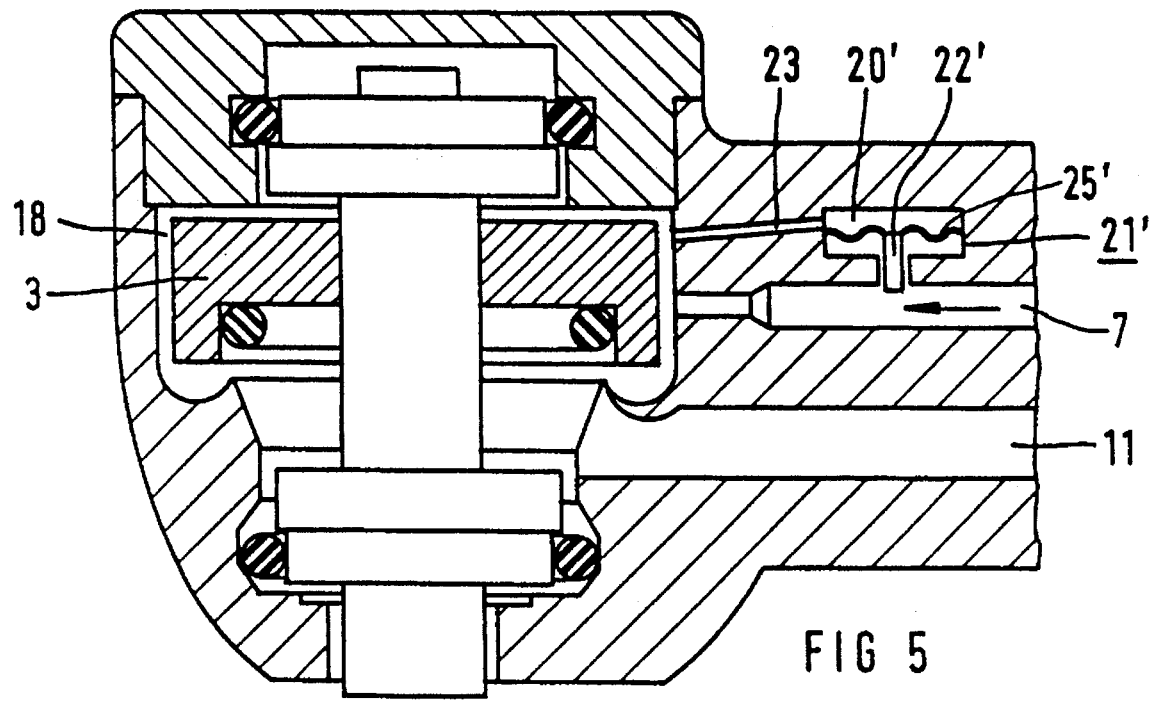
FIG. 5 is a cross sectional view with portions in elevation for purposes of illustration of a third embodiment of the present invention of the control means.
Figure 6:
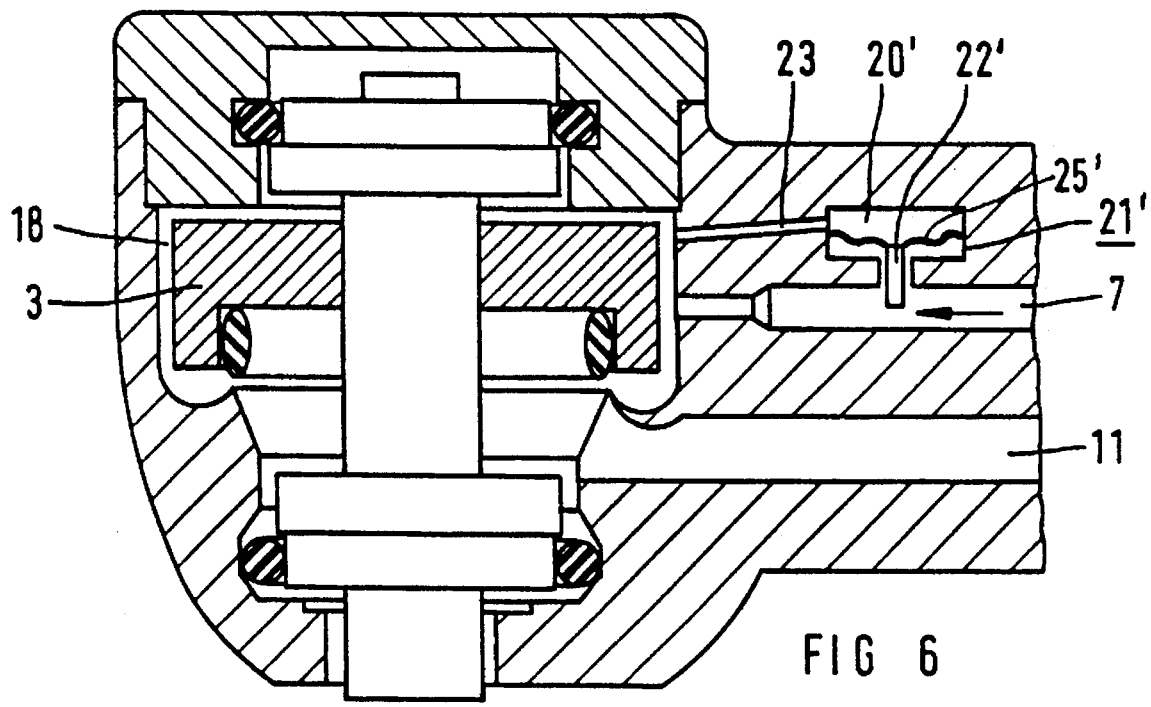
FIG. 6 is a cross sectional view of the embodiment of FIG. 5 with the control means constricting the cross section of the exhaust channel and also constricting the cross section of the inlet channel to the nozzle.

A third embodiment is illustrated in FIGS. 5 and 6. In this embodiment, the diaphragm valve 21' is arranged so that the control element 22', which is connected to the diaphragm 25', projects into a delivery channel 7 for the driving air. Here, too, changes in the pressure of the rotor chamber 18 act via a connecting channel 23 and chamber 20' on the diaphragm valve 21', which influences the driving airstream for the purpose of speed regulation. When, for example with increasing speed, the pressure in the rotor chamber 18 rises, the driving air delivery is slightly throttled, the result thereof being that this throttling opposes a further increase in the speed. The analogous case also applies given a decreasing speed.

Although various minor modifications may be suggested by those versed in the art, it should be understood that I wish to embody within the scope of the patent granted hereon all such modifications as reasonably and properly come within the scope of my contribution to the art.

I claim:

1. In a dental turbine drive containing a rotor disk being mounted for rotation by bearings in a rotor disk chamber of a housing, said rotor disk having turbine blades being chargeable with compressed air via a drive air nozzle connected to an inlet air channel, said housing having an exhaust air channel, the improvements comprising first means for throttling air flow comprising an elastic control element being arranged at the rotor disk in the flow path of the exhaust air, said control element deforming under the influence of a centrifugal force dependent on the speed of the rotor to constrict the effective flow cross section with increased speeds and to enlarge the effective flow cross section with decreasing speeds so that the air pressure in the rotor disk chamber facing toward the air drive nozzle raises or drops corresponding to the throttling effect and additional means for aiding the first means including a part of the rotor chamber facing toward the drive air nozzle being connected via a channel to an additional chamber that at least is partially limited by a second element that yields under pressure so that a change in pressure in the rotor disk chamber acts on said second element and produces a movement of said second element that supports the effect of the control element.

2. In a dental turbine drive according to claim 1, wherein the second element is an elastic membrane.

3. In a dental turbine drive according to claim 2, wherein the control element is an elastic ring received in a recess on a side of the rotor disk facing an exhaust air passage, said elastic ring expanding in an axial direction inside said recess on the basis of the centrifugal force dependent on the increase in speed, said ring being covered toward the outflow side by said elastic membrane, said additional chamber being formed by said membrane, ring and rotor disk and being connected to the rotor chamber via channels extending axially in said rotor disk.

4. In a dental turbine drive according to claim 3, wherein the membrane is prestressed to press against said control element.

5. In a dental turbine drive according to claim 4, wherein the membrane is formed of spring steel.

6. In a dental turbine drive according to claim 3, wherein the membrane is mechanically connected to the control element.

7. In a dental turbine drive according to claim 6, wherein the membrane and control element are constructed as a single one-piece member.

8. In a dental turbine drive according to claim 1, wherein the additional chamber is a pressure chamber for a diaphragm valve disposed in the housing spaced from the rotor disk chamber, said channels connecting said pressure chamber to the rotor disk chamber, said second element being a diaphragm having a control member for varying the effective cross section of one of said exhaust air channel and inlet air channel in response to pressure changes in the rotor chamber.

9. In a dental turbine drive according to claim 8, wherein said control member extends into the exhaust air channel to restrict the cross section of the exhaust air channel in response to increased pressure in the rotor chamber.

10. In a dental turbine drive according to claim 8, wherein the control member extends into the inlet air channel for the driving air to constrict the inflow of air in response to increases in pressure in the rotor chamber.

11. In a dental turbine drive according to claim 1, wherein the control element is an elastic ring disposed in a recess on a face of the rotor disk facing toward the exhaust air channel, said additional chamber and second element are part of a diaphragm valve arranged in a non-rotating part of the housing, said diaphragm valve having a diaphragm forming the second element, said diaphragm having a control member for varying the effective cross section of a channel extending to the rotor chamber in response to changes in the pressure in said rotor chamber.

* * * * *